(12) United States Patent
Caparso et al.

(10) Patent No.: US 10,137,312 B2
(45) Date of Patent: Nov. 27, 2018

(54) METHODS OF IMPROVING A PATIENTS RECOVERY AFTER A NEURO-ISCHEMIC EVENT

(71) Applicant: Autonomic Technologies, Inc., Redwood City, CA (US)

(72) Inventors: Anthony V. Caparso, Avon, OH (US); Benjamin D. Pless, Atherton, CA (US)

(73) Assignee: AUTONOMIC TECHNOLOGIES, INC., Mountain View, CA (US)

( * ) Notice: Subject to any disclaimer, the term of this patent is extended or adjusted under 35 U.S.C. 154(b) by 0 days.

(21) Appl. No.: 15/286,907

(22) Filed: Oct. 6, 2016

(65) Prior Publication Data

US 2017/0095676 A1 Apr. 6, 2017

Related U.S. Application Data

(60) Provisional application No. 62/237,754, filed on Oct. 6, 2015.

(51) Int. Cl.
| | |
|---|---|
| *A61N 5/06* | (2006.01) |
| *A61N 1/36* | (2006.01) |
| *A61N 1/05* | (2006.01) |
| *A61N 2/00* | (2006.01) |
| *A61F 7/00* | (2006.01) |

(52) U.S. Cl.
CPC .............. *A61N 5/0618* (2013.01); *A61F 7/00* (2013.01); *A61N 1/0529* (2013.01); *A61N 1/36* (2013.01); *A61N 1/36082* (2013.01); *A61N 2/006* (2013.01); *A61N 5/0622* (2013.01)

(58) Field of Classification Search
CPC ........ A61N 5/0618; A61N 1/36; A61N 2/006; A61N 1/36082; A61N 1/0529; A61F 7/00
See application file for complete search history.

(56) References Cited

U.S. PATENT DOCUMENTS

| | | | |
|---|---|---|---|
| 2010/0004717 A1* | 1/2010 | Kilgard | A61N 1/36014 607/59 |
| 2011/0190668 A1 | 8/2011 | Mishelevich | |
| 2012/0016434 A1* | 1/2012 | Lamensdorf | A61N 1/36082 607/45 |
| 2013/0190838 A1* | 7/2013 | Caparso | A61N 1/36071 607/46 |
| 2013/0317580 A1* | 11/2013 | Simon | A61N 1/40 607/115 |
| 2014/0276195 A1* | 9/2014 | Papay | A61B 5/0484 600/554 |
| 2015/0265830 A1* | 9/2015 | Simon | A61N 1/0456 600/13 |

* cited by examiner

*Primary Examiner* — Catherine Voorhees
(74) *Attorney, Agent, or Firm* — Tarolli, Sundheim, Covell & Tummino LLP

(57) ABSTRACT

In certain aspects, the present disclosure is directed to a method of improving a patient's recovery after a neuro-ischemic event. The method can include identifying a patient who has suffered a neuro-ischemic event, and stimulating, for a period of time, a parasympathetic structure in the patient's cranium before, during, and/or after the patient undergoes a task-oriented therapy to improve the patient's recovery.

23 Claims, 2 Drawing Sheets

METHODS OF IMPROVING A PATIENTS RECOVERY AFTER A NEURO-ISCHEMIC EVENT

CROSS-REFERENCE TO RELATED APPLICATIONS

The present application claims priority to U.S. Provisional Application No. 62/237,754 filed on Oct. 6, 2015, which is hereby incorporated by reference in its entirety.

TECHNICAL FIELD

The present disclosure relates to methods for improving a patient's recovery after a neuro-ischemic event by performing parasympathetic stimulation, for a period of time, before, during and/or after the patient undergoes a task-oriented therapy.

BACKGROUND

The World Health Organization's International Classification of Functioning, Disability, and Health organizes the effects of conditions such as stroke into problems in the "body structure and function dimension" and in the "activity and participation dimension." Body structure and function effects (known as "impairments"), such as hemiplegia, spasticity, and aphasia, are the primary neurological disorders that are caused by stroke. Activity limitations (also referred to as "disabilities") are manifested by reduced ability to perform daily functions, such as dressing, bathing, or walking. The magnitude of activity limitation is generally related to but not completely dependent on the level of body impairment (e.g. severity of stroke). Other factors that influence level of activity limitation include intrinsic motivation and mood; adaptability and coping skills; cognition and learning ability; severity and type of pre-existing and acquired medical co-morbidity; medical stability; physical endurance levels; effects of acute treatments; and the amount and type of rehabilitation training. Therapeutic interventions to improve sensorimotor performance after stroke vary considerably. Although there is emerging evidence that rehabilitation can be effective in improving both intrinsic motor control and functional status, systematic trials comparing the relative effectiveness of various motor control intervention types generally have been few in number and suboptimal in design.

SUMMARY

In certain aspects, the present disclosure is directed to a method of improving a patient's recovery after a neuro-ischemic event. The method can include identifying a patient who has suffered a neuro-ischemic event, and stimulating, for a period of time, a parasympathetic structure in the patient's cranium before, during, and/or after the patient undergoes a task-oriented therapy to improve the patient's recovery.

In certain aspects, the present disclosure is directed to another method of improving a patient's recovery after a neuro-ischemic event. The method can include identifying a patient who has suffered a neuro-ischemic event, and stimulating a parasympathetic structure in the patient's cranium prior to the patient undergoing a task-oriented therapy to improve the patient's recovery. The parasympathetic structure can be stimulated for the entire duration of the task-oriented therapy.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1:
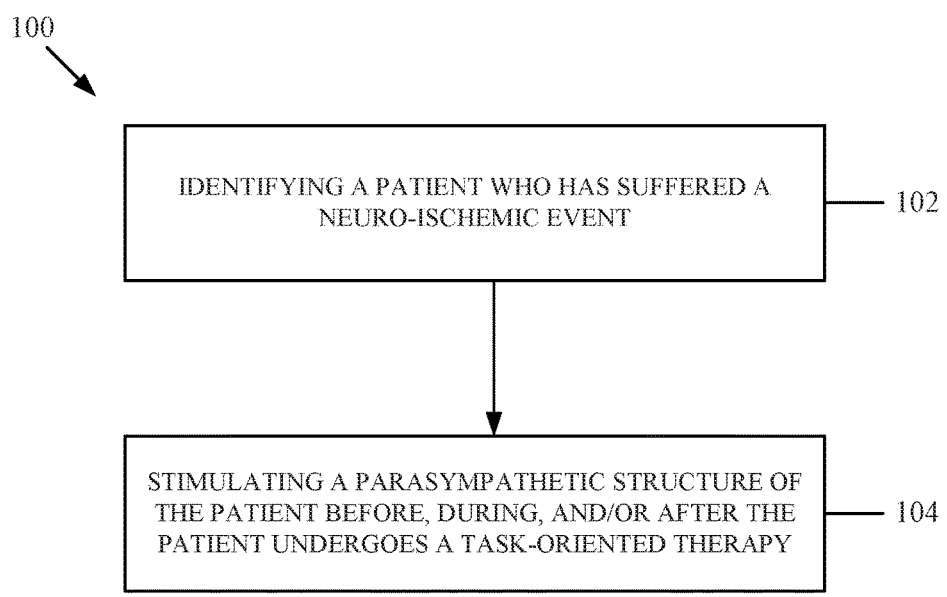
FIG. 1 is a process flow diagram showing a method of improving a patient's recovery after a neuro-ischemic event according to an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items. For example, the term "A and/or B" can include A alone, B alone, or A and B together.

As used herein, phrases such as "between X and Y" and "between about X and Y" can be interpreted to include X and Y.

As used herein, phrases such as "between about X and Y" can mean "between about X and about Y".

As used herein, phrases such as "from about X to Y" can mean "from about X to about Y".

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will also be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the terms "stimulation," "stimulated," or "stimulating" can refer to any artificial input that causes one or more neuromodulatory effects (e.g., excitation/activation, inhibition, conduction block, modulation of response to other inputs, or the like) in at least a portion of a parasympathetic structure in a patient's cranium. The stimulation can be electrical stimulation, magnetic stimulation, optical stimulation, thermal stimulation, electromagnetic stimulation, or the like. For example, an electrode or other therapy delivery device can be placed in contact (e.g., direct contact) or communication (e.g., electrical communication) with the parasympathetic structure to apply a therapy signal, such as an electrical signal, to the parasympathetic structure.

As used herein, the term "patient" can be used interchangeably with "subject" and refer to any warm-blood organism including, but not limited to, human beings, pigs, rats, mice, dogs, goats, sheep, horses, monkeys, apes, rabbits, cattle, etc.

As used herein, the term "electrical communication" can refer to the ability of a generated electric field to be transferred to, or have a biological effect on (e.g., action potential generation), a parasympathetic structure. In some instances, the generated electric field can be directly transferred to a parasympathetic structure (e.g., via an electrode that is connected to a wire or lead). In other instances, the generated electric field can be wirelessly transferred to a parasympathetic structure.

As used herein, the terms "improve" or "improving" when referring to a patient's recovery can mean one or more measurable (e.g., objective or subjective) improvements of at least one variable in a patient (e.g., a patient having suffered a neuro-ischemic event) as compared to a baseline or control value(s). Variables in which an improvement can be measured include, but are not limited to, basic self needs (e.g., bathing, cooking, eating, dressing, grooming, writing, using a computer, holding a conversation) and more complex tasks, such as complex reasoning, memory, judgment and driving. Other methods for measuring improvements in a patient's recovery (from a neuro-ischemic event) are known in the art. In some instances, the baseline or control value(s) can be obtained from an apparently healthy subject (e.g., a subject who has not suffered from a neuro-ischemic event) or a population of apparently healthy subjects. In other instances, the baseline or control value(s) can be obtained from a patient (or population of patients) before the patient(s) experience(s) a neuro-ischemic event. In still other instances, the baseline or control value(s) can include measurements, taken at various times, from a patient (or population of patients) that has/have suffered from a neuro-ischemic event.

As used herein, the terms "task-oriented therapy", "task-specific training", and "occupational therapy" can be used interchangeably and refer to an activity or training that involves practicing real-life skills or tasks (e.g., walking, answering a telephone) with the intention of acquiring or reacquiring the skill or task. The tasks can be challenging, progressively adapted, and involve active participation. Such tasks can include repetitive training where, for example, a task is divided into component parts and then reassembled into an overall task. The tasks can be specific to the upper extremity, lower extremity, or both.

As used herein, the term "physical therapy" can refer to the treatment of physical dysfunction or injury by the use of therapeutic exercise and the application of modalities, intended to restore or facilitate normal function or development. For example, the term can refer to strength training involved in regaining strength, coordination, balance and control of patient movement.

As used herein, the terms "cognitive therapy" and "cognitive rehabilitation" can be used interchangeably and refer to therapy to regain executive function, such as executing everyday actions, a sequence of actions, planning a task, beginning a task, knowing when one has completed a task, etc. Cognitive therapy incorporates elements of memory, processing speed, attentions and also deals with emotional, behavioral and cognitive aspects as well.

Relevant Neurophysiology

A brief discussion of the pertinent neurophysiology is provided to assist the reader with understanding certain aspects of the present disclosure.

The nervous system is divided into the somatic nervous system and the autonomic nervous system (ANS). In general, the somatic nervous system controls organs under voluntary control (e.g., skeletal muscles) and the ANS controls individual organ function and homeostasis. For the most part, the ANS is not subject to voluntary control. The ANS is also commonly referred to as the visceral or automatic system. The ANS can be viewed as a "real-time" regulator of physiological functions that extracts features from the environment and, based on that information, allocates an organism's internal resources to perform physiological functions for the benefit of the organism, e.g., responds to environment conditions in a manner that is advantageous to the organism.

The ANS conveys sensory impulses to and from the central nervous system to various structures of the body such as organs and blood vessels, in addition to conveying sensory impulses through reflex arcs. For example, the ANS controls constriction and dilatation of blood vessels; heart rate; the force of contraction of the heart; contraction and relaxation of smooth muscle in various organs such as the lungs, stomach, colon, and bladder; visual accommodation; and secretions from exocrine and endocrine glands, etc.

The parasympathetic nervous system (PNS) is part of the ANS and controls a variety of autonomic functions including, but not limited to, involuntary muscular movement and glandular secretions from the eyes, salivary glands, bladder, rectum and genital organs.

The sphenopalatine ganglion (SPG), also called the pterygopalatine ganglion, is part of the PNS and is located within the pterygopalatine fossa (PPF). The PPF is bounded anteriorly by the maxilla, posteriorly by the medial plate of the pterygoid process and greater wing of the sphenoid process, medially by the palatine bone, and superiorly by the body of the sphenoid process. Its lateral border is the pterygomaxillary fissure, which opens to the infratemporal fossa.

The SPG is a large, extra-cranial parasympathetic ganglion. The SPG is a complex neural ganglion with multiple connections, including autonomic, sensory and motor. The maxillary branch of the trigeminal nerve and the nerve of the pterygoid canal, also known as the vidian nerve (VN) sends neural projections to the SPG. The fine branches from the maxillary nerve—known as the pterygopalatine nerves or sphenopalatine nerves (SPN)—form the sensory component of the SPG. The SPN pass through the SPG and do not synapse. The greater petrosal nerve (GPN) (discussed below) carries the preganglionic parasympathetic axons from the superior salivary nucleus to the SPG. These fibers synapse onto the postganglionic neurons within the SPG. The deep petrosal nerve (DPN) (discussed below) connects the superior cervical sympathetic ganglion to the SPG and carries postganglionic sympathetic axons that again pass through the SPG without any synapses. The DPN and the GPN carry sympathetic and parasympathetic fibers, respectively. The greater and lesser palatine nerves are branches of the SPG that carry both general sensory and parasympathetic fibers.

The DPN and the GPN join together just before entering the pterygoid canal to form the VN. The DPN is given off from the carotid plexus and runs through the carotid canal lateral to the internal carotid artery. It contains postganglionic sympathetic fibers with cell bodies located in the superior cervical ganglion. It then enters the cartilaginous substance, which fills the foramen lacerum, and joins with the greater superficial petrosal nerve to form the VN. The GPN then passes through the SPG without synapsing and joins the postganglionic parasympathetic fibers in supplying the lacrimal gland, the nasal mucosa, and the oral mucosa. The GPN is given off from the geniculate ganglion of the facial nerve. It passes through the hiatus of the facial canal, enters the cranial cavity, and runs forward beneath the dura mater in a groove on the anterior surface of the petrous portion of the temporal bone. The GPN enters the cartilaginous substance, which fills the foramen lacerum, and then joins with the DPN to form the VN. The lesser petrosal nerve carries parasympathetic (secretory) fibers from both the tympanic plexus and the nervus intermedius to the parotid gland.

The VN projects to the PPF through the vidian canal. The VN contains two of the three neural roots of the SPG, parasympathetic and sympathetic. The third neural root of the SPG includes sensory fibers that derive from the second division of the trigeminal nerve, also called maxillary nerve. The maxillary nerve connects to the SPG through the SPN and this causes the SPG to suspend form the maxillary nerve within the PPF.

The VN is housed within the vidian canal, which is posterior to the SPG. The VN connects to the SPG and contains parasympathetic fibers, which synapse in the SPG, sensory fibers that provide sensation to part of the nasal septum, and also sympathetic fibers. The SPN are sensory nerves that connect the SPG to the maxillary nerve. The SPN traverse through the SPG without synapsing and proceed to provide sensation to the palate. The SPN suspend the SPG in the PPF.

Overview

The present disclosure relates to methods for improving a patient's recovery after a neuro-ischemic event by performing parasympathetic stimulation, for a period of time, before, during and/or after the patient undergoes a task-oriented therapy. Advantageously, the methods of the present disclosure can improve the patient's recovery after the neuro-ischemic event, and that such recovery can include enhancing the patient's neural plasticity through increased cerebral blood flow (e.g., by dilating one or more cerebral blood vessels) prior to, during, and/or after therapy to the area with a neurological deficit resulting from the neuro-ischemic event. Consequently, the methods of the present disclosure can improve the patient's gross and fine motor function, cognitive function, speech function, or any suitable combination thereof.

Methods

One aspect of the present disclosure can include methods 100 and 200 (FIGS. 1 and 2, respectively) for improving a patient's recovery after a neuro-ischemic event. The methods 100 and 200 are illustrated as process flow diagrams with flowchart illustrations. For purposes of simplicity, the methods 100 and 200 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 100 and 200.

Figure 2:
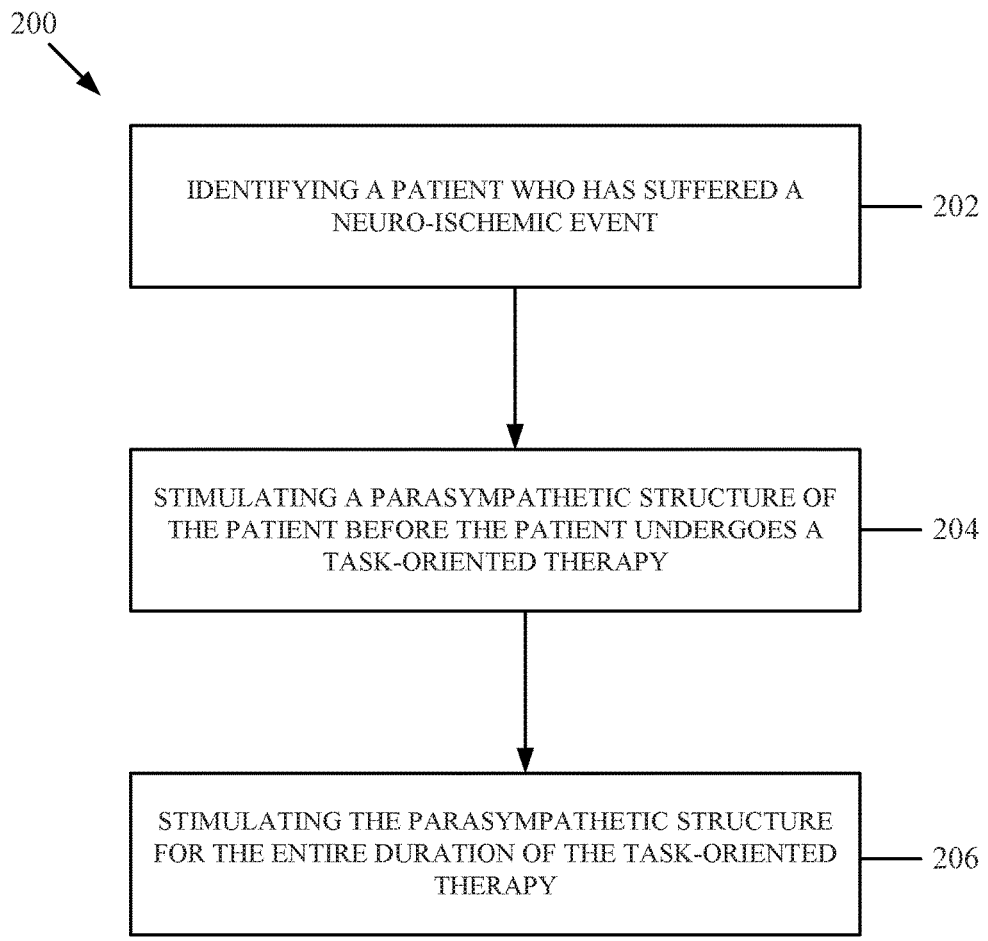
FIG. 2 is a process flow diagram showing a method of improving a patient's recovery after a neuro-ischemic event according to another aspect of the present disclosure.

Referring to FIG. 1, the method 100 can include the steps of: identifying a patient who has suffered a neuro-ischemic event (Step 102); and stimulating, for a period of time, a parasympathetic structure in the patient's cranium before, during, and/or after the patient undergoes a task-oriented therapy to improve the patient's recovery after the neuro-ischemic event (Step 104).

The patient identified at Step 102 may have suffered any one or combination of neuro-ischemic events that result(s) in inadequate blood flow to a neural structure, such as the brain, of the patient. Non-limiting examples of neuro-ischemic events can include a stroke (e.g., ischemic stroke and a hemorrhagic stroke) and a transient ischemic attack (TIA). Methods for identifying patients suffering from a neuro-ischemic event are known to those skilled in the art. For example, methods for identifying a patient who has suffered from a stroke can include assessing a patient for such symptoms as face drooping, arm weakness, and speech difficulty. Additionally, methods for identifying a patient who has suffered from a TIA can include assessing a patient for such symptoms as vision changes, trouble speaking, confusion, balance issues, numbness, weakness, tingling, and muscular weakness on one side of the body.

At Step 104, the parasympathetic structure can be stimulated for a period of time before, during, and/or after the patient undergoes a task-oriented therapy. In some instances, one or more parasympathetic structures located in the PPF of the patient's cranium can be stimulated. For example, the parasympathetic structure can include a SPG, a SPN, a VN, a GPN, a nasopalatine nerve, or any suitable combination thereof. Stimulation can be accomplished using an electrode or other therapy delivery device that is placed in contact (e.g., direct contact) or communication (e.g., electrical communication) with the parasympathetic structure. Examples of electrodes and therapy delivery devices that may be used to stimulate the parasympathetic structure are known to those skilled in the art and can include, for example, those that are commercially available from Autonomic Technologies, Inc. (Redwood City, Calif.), Brainsgate (Caesarea, Israel) and Oculeve/Allergan (Parsippany, N.J.), as well as certain deep brain stimulation devices (e.g., used for stimulating the ventral lateral hypothalamus. Similarly, surgical methods for placing and/or implanting electrodes and therapy delivery devices are known to those skilled in the art, examples of which can include percutaneous, subcutaneous, trans-oral, and trans-nasal approaches.

Stimulation of the parasympathetic structure can occur before, during, and/or after the patient undergoes a task-oriented therapy. In some instances, the task-oriented therapy can include any activity that drives one or more specific neurological functions, such as picking up a cup and bringing it to the patient's mouth or picking up a telephone and placing it on the ear. In one example, the task-oriented therapy can include a physical therapy, such as a motor task. Non-limiting examples of motor tasks include exposure to orthostatic or gravitational stress, such as: intermittent sitting or standing; gait retraining; walking treadmill training; upper limb training; constraint-induced movement therapy (CMT); task-specific training; and progressive resistance exercises. In another example, the task-oriented therapy can include a cognitive therapy, such as a cognitive task or a speech task. Non-limiting examples of speech tasks can include tasks that address a patient's difficulty in understanding or producing speech correctly (aphasia), slurred speech consequent to weak muscles (dysarthria), difficulty in programming oral muscles for speech production (apraxia), reading and writing. Non-limiting examples of cognitive tasks can include attention tasks, memory training, gaming (e.g., virtual reality) and problem solving. It will be appreciated that two or more different therapies can be performed by the patient either consecutively or at the same time. In one example of the method 100, the parasympathetic structure can be simulated while the patient simultaneously undergoes a task-oriented therapy.

In certain aspects, the parasympathetic structure can be stimulated at a frequency, pulse-width, an amplitude, and for a time sufficient to improve the patient's recovery from a neuro-ischemic event. In some instances, the parasympathetic structure can be stimulated at a frequency of between about 0.5 Hz to about 1 KHz, between about 0.5 Hz to about 500 Hz, or between about 0.5 Hz to about 100 Hz (e.g., between about 0.5 Hz to about 60 Hz). In other instances, the parasympathetic structure can be stimulated at a pulse-width of between about 10 microseconds (μsec) to about 1000 μsec, about 100 μsec to about 500 μsec, or about 200 μsec to about 300 μsec. In other instances, the parasympathetic structure can be stimulated at an amplitude of between about 0 mA to about 10 mA, about 2 mA to about 8 mA, or about 4 mA to about 6 mA.

Where the parasympathetic structure is stimulated before the patient undergoes a task-oriented therapy, stimulation can be applied for a period of time of about 5 seconds to about 1 hour, about 5 minutes to about 55 minutes, about 10 minutes to about 50 minutes, about 15 minutes to about 45 minutes, about 20 minutes to about 40 minutes, or about 25 minutes to about 35 minutes prior to commencement of the task-oriented therapy. In one example, the parasympathetic structure is stimulated before the patient undergoes a task-oriented therapy for a period of time of about 10 seconds to about 30 seconds (e.g., about 20 seconds) prior to commencement of the task-oriented therapy. In another example, the parasympathetic structure is stimulated before the patient undergoes a task-oriented therapy for a period of time of about 10 minutes prior to commencement of the task-oriented therapy.

Where the parasympathetic structure is stimulated after the patient undergoes a task-oriented therapy, stimulation can be applied for a period of time of about 5 seconds to about 1 hour, about 5 minutes to about 55 minutes, about 10 minutes to about 50 minutes, about 15 minutes to about 45 minutes, about 20 minutes to about 40 minutes, or about 25 minutes to about 35 minutes after commencement of the task-oriented therapy.

In certain aspects, the parasympathetic structure can be stimulated for the entire duration of the task-oriented therapy, or only a portion of the task-oriented therapy, depending upon the nature of the task-oriented therapy. As such, the duration of stimulation during the task-oriented therapy can be a few seconds, minutes or hours.

It will be appreciated that stimulation can be applied before and during the task-oriented therapy, before and after the task-oriented therapy, or during and after the task-oriented therapy.

In terms of improving the patient's recovery according to the method 100, such recovery can comprise enhancing the patient's neural plasticity through increased cerebral blood flow during therapy. Recovery can comprise enhancing patient neurological recovery through a combination of tasks that specifically activate a given neurological are (or areas) (e.g., where a neurological deficit occurs as the result of a neuro-ischemic event) and enhanced blood flow to the area(s) with the neurological deficit. This combination of events can enhance the neural plasticity and thus strengthen neurological circuits to reduce the neurological deficit(s).

For example, the recovery can include dilating a cerebral blood vessel of the patient while also improving the patient's gross and fine motor function, cognitive function, speech function, or any suitable combination thereof. As such, stimulating a parasympathetic structure of the patient can increase cerebral blood flow to an area of a neurological deficit while the patient performs a task-oriented therapy (e.g., a motor, speech or cognitive task) that specifically activates the area of the neurological deficit.

Another aspect of the present disclosure can include a method 200 (FIG. 2) of improving a patient's recovery after a neuro-ischemic event. The method 200 can comprise the steps of: identifying a patient who has suffered a neuro-ischemic event (Step 202); stimulating a parasympathetic structure in the patient's cranium prior to the patient undergoing a task-oriented therapy (Step 204); and continuing to stimulate the parasympathetic structure while the patient is simultaneously undergoing the task-oriented therapy, for the entire duration of the task-oriented therapy, to improve the patient's recovery after the neuro-ischemic event (Step 206).

Although the methods 100 and 200 of the present disclosure can be performed at any suitable time after the neuro-ischemic event, in certain aspects, the methods are performed within the first six months after the neuro-ischemic event. Further, although the methods 100 and 200 can be performed for any suitable duration, preferably the methods are performed for at least one hour per day and at least five days per week for patients undergoing active rehabilitation.

From the above description of the present disclosure, those skilled in the art will perceive improvements, changes and modifications. Such improvements, changes, and modifications are within the skill of the art and are intended to be covered by the appended claims. All patents, patent applications, and publications cited herein are incorporated by reference in their entirety.

What is claimed is:

1. A method of improving a patient's recovery after a stroke or a transient ischemic attack, the method comprising the steps of:
   placing an electrode in electrical communication with a parasympathetic structure of a cranium of a patient who has suffered from a stroke or a transient ischemic attack;
   applying an electrical signal to the parasympathetic structure in the patient's cranium during the patient undergoing a task-oriented therapy to improve the patient's recovery after the stroke or the transient ischemic attack.

2. The method of claim 1, wherein applying an electrical signal to the parasympathetic structure during the patient undergoing a task-oriented therapy comprises applying the electrical signal while the patient simultaneously undergoes the task-oriented therapy.

3. The method of claim 1, wherein the task-oriented therapy is a physical therapy, a cognitive therapy, or a combination thereof.

4. The method of claim 1, wherein the stroke or the transient ischemic attack is a stroke.

5. The method of claim 4, wherein the stroke is an ischemic stroke.

6. The method of claim 4, wherein the stroke is a hemorrhagic stroke.

7. The method of claim 1, wherein the stroke or the transient ischemic attack is a transient ischemic attack.

8. The method of claim 1, wherein the parasympathetic structure is located in the pterygopalatine fossa (PPF) of the cranium.

9. The method of claim 8, wherein the parasympathetic structure is a sphenopalatine ganglion (SPG).

10. The method of claim 1, wherein the parasympathetic structure is a vidian nerve (VN), a greater petrosal nerve (GPN), a sphenopalatine nerve (SPN), a nasopalatine nerve, or any suitable combination thereof.

11. The method of claim 1, wherein to improve the patient's recovery after the stroke or the transient ischemic attack comprises improving the patient's motor function, improving the patient's cognitive function, improving the patient's speech function, or any suitable combination thereof.

12. The method of claim 1, wherein to improve the patient's recovery after the stroke or the transient ischemic attack comprises enhancing the patient's neural plasticity through increased cerebral blood flow during therapy.

13. The method of claim 1, wherein to improve the patient's recovery after the stroke or the transient ischemic attack comprises vasodilation of a cerebral blood vessel.

14. The method of claim 3, wherein undergoing physical therapy comprises performing a motor task, a speech task, a cognitive task, or any suitable combination thereof.

15. The method of claim 3, wherein undergoing physical therapy comprises the patient performing a motor task and wherein stimulating the parasympathetic structure in the patient's cranium increases cerebral blood flow.

16. The method of claim 1, wherein stimulating the parasympathetic structure in the patient's cranium occurs at a frequency between about 0.5 Hz to about 1 KHz, a pulse-width between about 10 µsec to about 1000 µsec, and an amplitude between about 0 mA and about 10 mA.

17. The method of claim 16, wherein stimulating the parasympathetic structure in the patient's cranium occurs at a frequency of between about 0.5 Hz to about 60 Hz.

18. The method of claim of 1, wherein placing an electrode in electrical communication with a parasympathetic structure comprises placing an electrode percutaneously, subcutaneously, trans-orally, or trans-nasally into electrical communication with the parasympathetic structure in the patient's cranium.

19. The method of claim 1, further comprising applying an electrical signal to the parasympathetic structure in the patient's cranium before and/or after the patient undergoes a task-oriented therapy.

20. The method of claim 19, wherein stimulating a parasympathetic structure before the patient undergoes the task-oriented therapy occurs for a duration of about 10 to 30 seconds.

21. The method of claim 20, wherein the duration is about 20 seconds.

22. The method of claim 1, further comprising continuing to apply an electrical signal to the parasympathetic structure while the patient is simultaneously undergoing the task-oriented therapy, for the entire duration of the task-oriented therapy, to improve the patient's recovery after the stroke or the transient ischemic attack.

23. The method of claim 19, wherein the electrical signal is applied to the parasympathetic structure before and/or after the patient undergoes the task-oriented therapy for about 5 seconds to about an hour.

* * * * *